United States Patent [19]
Aristides

[11] Patent Number: 5,928,158
[45] Date of Patent: Jul. 27, 1999

[54] MEDICAL INSTRUMENT WITH NERVE SENSOR

[76] Inventor: Arellano Aristides, 20 Sur 2539, Puebla, Mexico, 72500

[21] Appl. No.: 08/823,992

[22] Filed: Mar. 25, 1997

[51] Int. Cl.⁶ .................................................. A61B 5/05
[52] U.S. Cl. .................... 600/547; 600/554; 604/116; 606/32; 606/205
[58] Field of Search ..................... 600/118, 461, 600/464, 564, 567, 554, 587, 547, 550; 606/35, 23, 32, 170, 174, 705, 39; 604/116

[56] References Cited

U.S. PATENT DOCUMENTS

| | | | |
|---|---|---|---|
| 2,704,064 | 3/1955 | Fizzell et al. | 600/554 |
| 4,515,168 | 5/1985 | Chester et al. | 600/554 |
| 4,962,766 | 10/1990 | Herzon | 600/554 |
| 5,080,104 | 1/1992 | Marks et al. | 600/461 |
| 5,284,154 | 2/1994 | Raymond et al. | 600/554 |
| 5,775,331 | 7/1998 | Raymond et al. | 600/554 |
| 5,779,642 | 7/1998 | Nightengale | 600/554 |
| 5,830,151 | 11/1998 | Hadzic et al. | 600/554 |

*Primary Examiner*—Richard J. Apley
*Assistant Examiner*—Justine R. Yu

[57] ABSTRACT

An improved surgical instrument which is used for cutting of tissue. The instrument includes a sensor which identifies nerves within the patient which are proximate to the cutting member of the instrument. The entire assembly is hand held and includes both a surgical cutter such as a scalpel blade, scissors, or laser scalpel, as well as the electronics to stimulate nerves within the patient. The electronics monitor is positioned near the tip of the instrument to warn the surgeon of a proximate nerve so that the nerves are not inadvertently severed. In one embodiment of this invention, the scissors are incapacitated when a nerve is sensed to prevent an accidental cutting of the nerve.

3 Claims, 5 Drawing Sheets

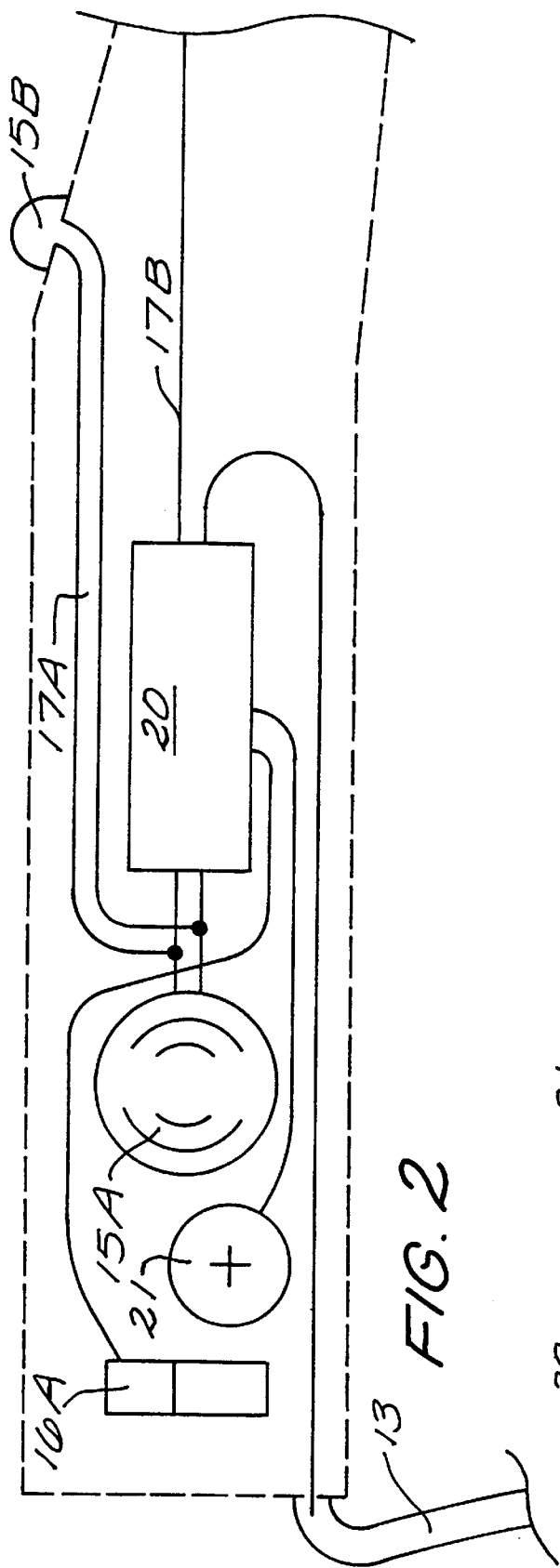
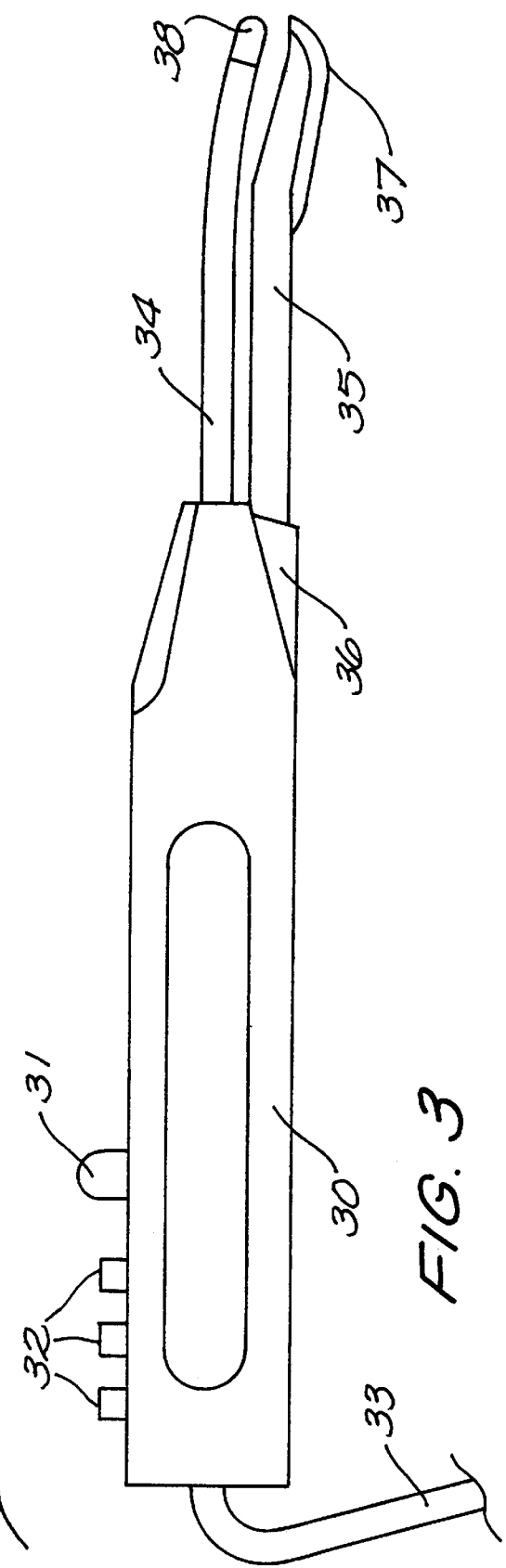
FIG. 2
FIG. 3

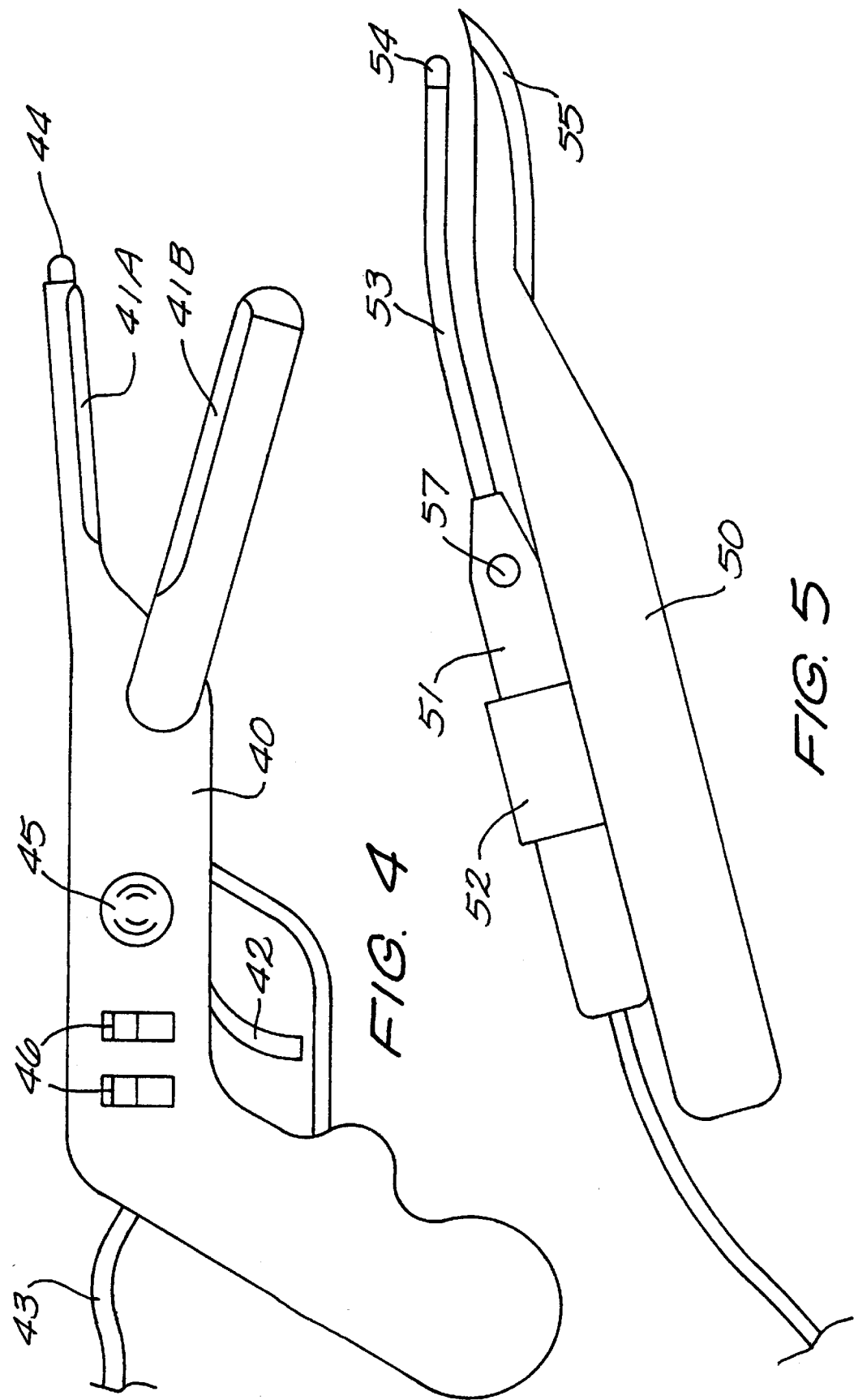

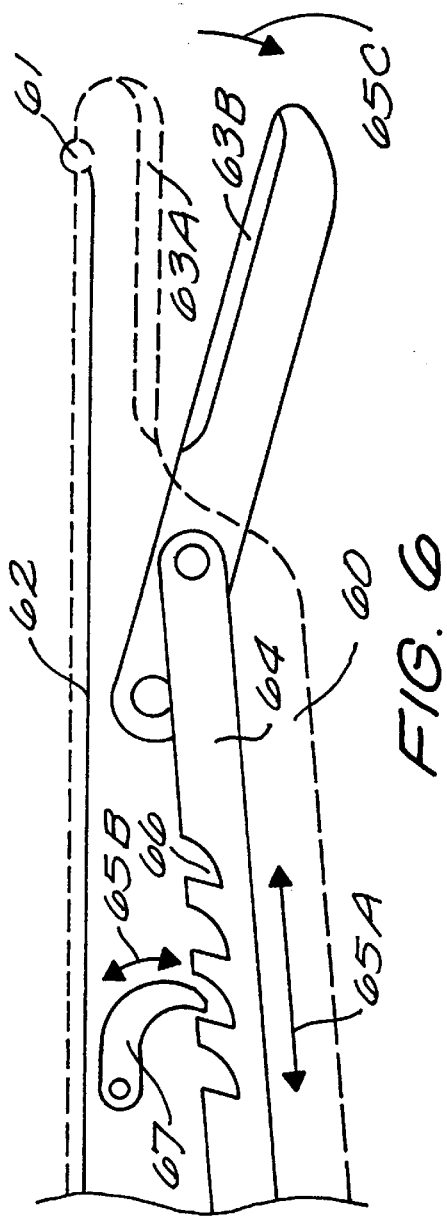
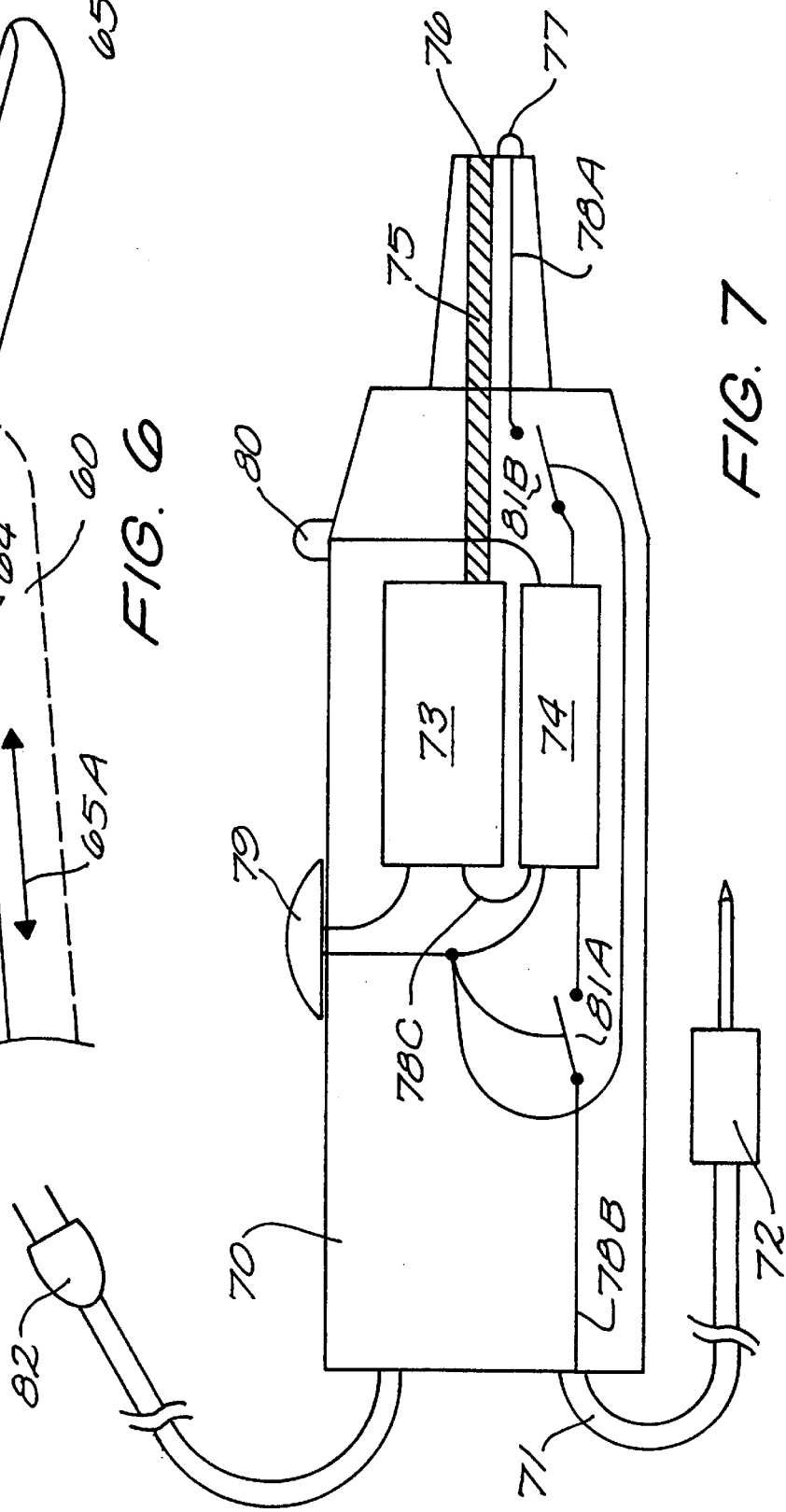
FIG. 6
FIG. 7

MEDICAL INSTRUMENT WITH NERVE SENSOR

BACKGROUND

This invention relates generally to the medical field and more particularly to surgical instruments.

Surgery continues to be one of the riskiest medical procedures. Each patient's anatomy differs ever so slightly, requiring the surgeon to be ever vigilant to these differences so that the intended result is accomplished.

The positioning of nerves within the body is one example of how the internal anatomy differs from patient to patient. While these differences may be ever so slight, if the surgeon fails to properly identify a nerve and cuts it, then catastrophic affects can occur. When a nerve is severed, the range of consequences extends from lack of feeling on that part of the body to loss of muscle control.

Because of these affects, a variety of instruments have been developed to assist the surgeon in identifying the location of nerves. One such device is U.S. Pat. No. 4,962,766, entitled "Nerve Locator and Stimulator" issued to Herzon on Oct. 16, 1990. This apparatus is a hand-held device which permits the surgeon to identify the location of nerves on external to the skin. This is accomplished by providing an electrical signal into the body and then monitoring the skin for this signal.

While this approach does effectively identify the general location of the nerve at the skin level, during the surgery, the exact location must still be identified before any dissection or cutting of the tissue can be done.

It is clear that there is a significant need for an efficient and real time nerve sensing apparatus.

SUMMARY OF THE INVENTION

The invention involves an improved surgical instrument which is used for cutting of tissue. In this context, a variety of surgical instruments are contemplated including: scalpels with blades, scissors, and laser scalpels. Those of ordinary skill in the art readily recognize a variety of other such instruments.

In this invention, the surgical instrument includes a sensor which identifies nerves within the patient which are proximate to the cutting member of the instrument. During the operation, and within a patient's body cavity, there is often a need to cut or dissect. During these procedures, the surgical instrument of the present invention provides, in a single hand-held instrument, the ability to both cut tissue and check for the presence of a nerve in the area being cut.

In this manner, the danger of accidentally cutting a nerve is minimized.

The entire assembly is hand held and includes both a surgical cutting mechanism such as a scalpel or scissors, as well as the electronics to stimulate nerves within the patient.

Those of ordinary skill in the art readily recognize a variety of mechanisms which are used for the cutting of tissue as well as a variety of electronic mechanisms which are used to stimulate and identify nerves within the human body. One such device is U.S. Pat. No. 4,962,766, entitled "Nerve Locator and Stimulator" issued to Herzon on Oct. 16, 1990, incorporated hereinto by reference.

In general, the electronic identification of a nerve location requires the application of a pre-defined signal to a remote part of the body. The tissue in the area of the surgery is then monitored for this signal which will be transmitted substantially intact through the nerves of the body. The same signal, when communicated through tissue degrades. The level of degradation of the signal is an indication of the proximity of the nerve.

Should the proximity of the nerve be detected, then an alarm is provided to the surgeon. This alarm takes a variety of forms including lights and buzzers.

The nerve sensor includes an exposed "contact" positioned preferably near the tip of the instrument to warn the surgeon of a proximate nerve so that the nerves are not inadvertently severed. The contact, in this context, is an exposed metal contact which in some embodiments are part of the cutting mechanism itself. In these embodiments. as example, the tip of the scalpel is adapted to become the contact for sensing the nerve. The surgeon, probes with the tip of the scalpel before cutting to identify where a nerve may be.

Another embodiment of the invention positions the nerve sensing contact on the dull side or back of the scalpel to allow this area to be safely used as a probe.

Still another embodiment of the invention has the nerve sensing electronics with probe attachable to a scalpel or other cutting instrument. The probe has an exposed contact and extends so that the exposed contact is proximate to the cutting portion of the surgical instrument.

In one embodiment of this invention, the scissors are incapacitated when a nerve is sensed to prevent an accidental cutting of the nerve. Incapacitation of the scissors is accomplished through a variety of mechanisms including a locking mechanism which engages the blades when a nerve is sensed.

In this embodiment, a manual over-ride of the locking mechanism is provide so that the surgeon can selectively cut nerves which require cutting during the procedure.

The invention, together with various embodiments thereof, will be more fully explained by the attached drawings and the following descriptions.

DRAWINGS IN BRIEF

FIG. 2 is an electrical schematic of the preferred embodiment.

FIG. 3 is a side view of an alternative embodiment of the invention.

FIG. 4 is a side view of an alternative embodiment of the invention as used within a scissors application.

FIG. 5 is a top view of an alternative embodiment of the invention in which the nerve sensor is attached to a scalpel.

FIG. 6 is a close up view of the scissors tip incorporating the automatic catch mechanism.

FIG. 7 is a schematic of an embodiment of the invention as used in a laser scalpel application.

DRAWINGS IN DETAIL

Figure 1:
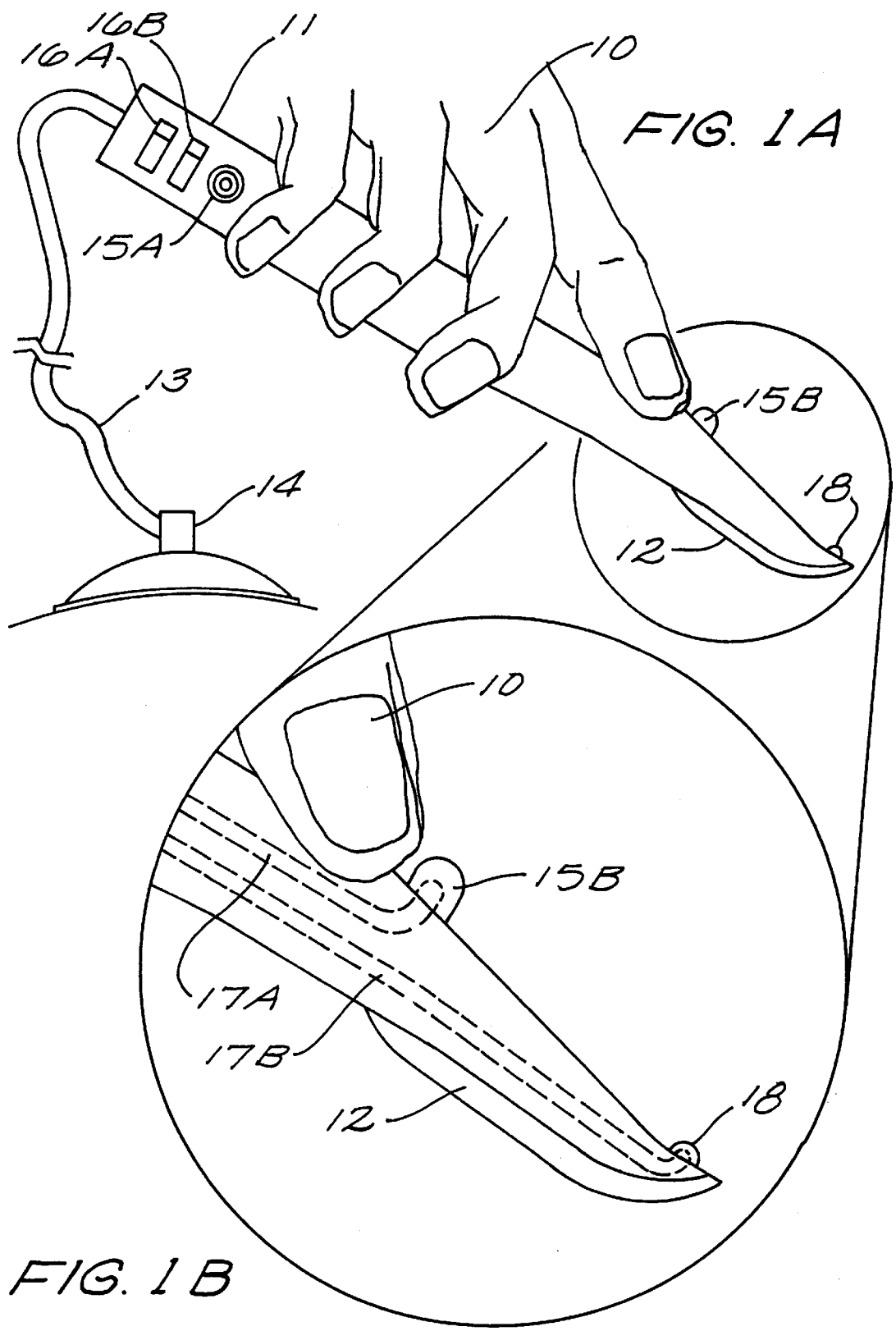
FIG. 1A is side view of the preferred embodiment in use by a surgeon.
FIG. 1B is a close up illustration of the tip of the preferred embodiment first illustrated in FIG. 1A.

FIG. 1A is side view of the preferred embodiment in use by a surgeon.

Surgeon 10 grasps housing 11 which, in this embodiment, contains the entire mechanism. Housing 11 is adapted at its distal end to include a scalpel blade 12. Positioned near scalpel blade 12, and visible to surgeon 10, is alarm light 15B which is illuminated when a nerve is sensed.

Sensing of the nerve is through use of contact 18. Contact 18 is electrically isolated in this embodiment from the rest of instrument to provide for improved sensitivity.

In another embodiment of the invention, the cutting blade is electrically isolated from the rest of the instrument and an electrical lead communicates between the electronics unit and the blade; thereby making the entire blade the exposed contact for sensing of the nerve.

Within housing 11 is the electronic unit (not shown) which senses the proximity of a nerve using contact 18. Activation of the electronics unit is via switch 16A; the sensitivity of the sensing mechanism is defined by the surgeon through manipulation of switch 16B.

As discussed earlier, a pre-defined signal is communicated from the electronics unit to the patient via electrical lead 13 which is in electrical communication with the patient via patch 14. When a nerve is proximate to contact 18, in this embodiment, both light 15B is illuminated and an audio alarm is sounded via speaker 15A. In this manner, the surgeon is warned of the proximity of the nerve and can exercise greater care.

FIG. 1B is a close up illustration of the tip of the preferred embodiment first illustrated in FIG. 1A.

Operator 10 is able to manipulate the instrument manually and utilize blade 12 to cut tissue within the human body. The surgical site is inspected using contact 18 which communicates with the electronics unit (not shown) via electrical lead 17B.

Should a nerve be sensed, then the electronics unit activates light 15B using electrical lead 17A. The positioning of lamp 15B in close proximity to the cutting location quickly draws the surgeon's attention during the operation.

FIG. 2 is an electrical schematic of the preferred embodiment.

Housing 11 contains the entire electronics unit. Controller system 20 includes the circuitry for sensing of a nerve such as that shown in the Herzon patent. Power is supplied to the system via battery 21 which is connected to the controller system 20 via switch 16A.

A pre-defined signal is communicated from controller system 20 to the patient via electrical lead 13 and the controller system 20 monitors the contact via electrical lead 17B.

When a nerve is sensed as being proximate to the contact, speaker 15A is activated and lamp 15B is illuminated. While this embodiment uses these two mechanisms, audio and visual, to alert the surgeon, those of ordinary skill in the art readily recognize that various other mechanisms can be utilized.

FIG. 3 is a side view of an alternative embodiment of the invention.

Housing 30 contains an electronics unit similar to that discussed with relationship to FIG. 2. Switches 32 communicate with the electronics unit and alarm light 31 is provided to give a warning of a proximate nerve.

Electrical lead 33 provides contact with the patient for supplying the pre-defined signal which is to be sensed.

Sensing of the nerve uses probe 34 which terminates in an electrically isolated contact point 38. The surgeon, by pressing contact point 38 against the tissue, easily identifies if a nerve is near.

In this embodiment, scalpel 35 is affixed to housing 30 via connector 36. Scalpel 35 has cutting edge 37. The ability to remove the scalpel from the housing permits the surgeon to select the particular scalpel to be used for the procedure at hand.

In this embodiment, probe 34 is also removable from the housing. In use, the surgeon chooses the scalpel and the corresponding probe for attachment to housing 30. The instrument is, in this manner, customized to the particular needs of the surgeon.

FIG. 4 is a side view of an alternative embodiment of the invention as used within a scissors application.

In this embodiment, housing unit 40 includes a pair of blades 41A and 41B which are activated by the surgeon using trigger 42.

Sensing of the nerves is accomplished using contact 44 which is located at a distal end of blade 41A. The pre-defined signal is communicated to the patient via electrical lead 43 and speaker 45 is used to emit an audio alarm upon the sensing of a nerve proximate to contact 44. Switches 46 allow the surgeon to activate the sensing unit and to adjust its sensitivity.

This embodiment, scissors with sensor, is especially advantageous for endoscopic procedures which utilize scissors extensively for cutting tissue.

FIG. 5 is a top view of an alternative embodiment of the invention in which the nerve sensor is attached to a scalpel.

Scalpel 50 has mounting bracket 52 affixed thereto. Mounting bracket 52 is used to secure nerve sensor 51 thereto. Once secured to scalpel 50, nerve sensor 51 is properly positioned such that probe 53 places contact 54 proximate to scalpel blade 55.

In use, the surgeon contacts the site with contact 54, thereby permitting the nerve sensor 51 to determine if a nerve is near; light 57 warns the surgeon if a nerve is near. If the area is "clear", then the surgeon turns to using blade 55 of scalpel 50.

FIG. 6 is a close up view of the scissors tip incorporating the automatic catch mechanism.

Housing 60 includes rigid blade 63A and has attached to it, moveable blade 63B. Moveable blade 63B is connected to driving member 64 which moves in a lateral motion as indicated by arrow 65A. This lateral motion is translated into a side motion indicated by arrow 65C of moveable blade 63B. The side motion forces blades 63A and 63B to contact and cut tissue therebetween.

Exposed contact 61 is positioned to sense a nerve and communicates with the nerve sensing circuit (not shown) via electrical lead 62. When the sensing circuit senses the presence of a nerve, catch 67 is moved as indicated by arrow 65B to engage gears 66 on driving member 64. This engagement between catch 67 and gears 66 prevents driving member 64 from forcing blade 63B to move against blade 63A.

Movement of catch 67 is accomplished through a variety of mechanisms such as micro-solenoids and magnetics. Those of ordinary skill in the art readily recognize a variety of mechanisms which can be used in this context.

This safety measure, the locking of blades 63A and 63B, prevents the surgeon from inadvertently cutting a nerve due to lack of attention. An over-ride is provided which disengages the sensing circuity from catch 67. The over-ride is used then a nerve is to be intentionally severed.

FIG. 7 is a schematic of an embodiment of the invention as used in a laser scalpel application.

Housing 70 receives all of its energy via power source 82. This power is communicated to the laser generator 73 and the nerve sensing circuitry 74.

The nerve sensing circuitry 74 generates a signal which is communicated to the patient via lead 78B, lead 71 and needle contact 72. Monitoring for this signal is via contact 77 which communicates via lead 78A with the nerve sensing 74.

Laser scalpels can generate an electrical signal which could be harmful to the nerve sensing circuitry 74; hence, laser switch 79 is a two position switch. As laser switch 79 is depressed by the surgeon, it passes a first stage where the nerve sensing circuitry 74 is electrically isolated through the opening of switches 81A and 81B. Continued depression of laser switch 79 causes laser generator 73 to be activated and to generate a laser beam which is communicated via optical channel 75 to exit via laser port 76 to cause cutting and cauterizing of the patient.

In this manner, no electrical signals are allowed to reach the nerve sensing circuitry 74 while the laser generator 73 is activated.

As a further safety measure, this embodiment permits the nerve sensing circuit 74 to disable the laser generator 73 by transmitting a signal via lead 78C. This signal is generated when a nerve is sensed proximate to contact 77. At the same time, alarm light 80 is also activated by nerve sensing circuit 74.

Figure 8:
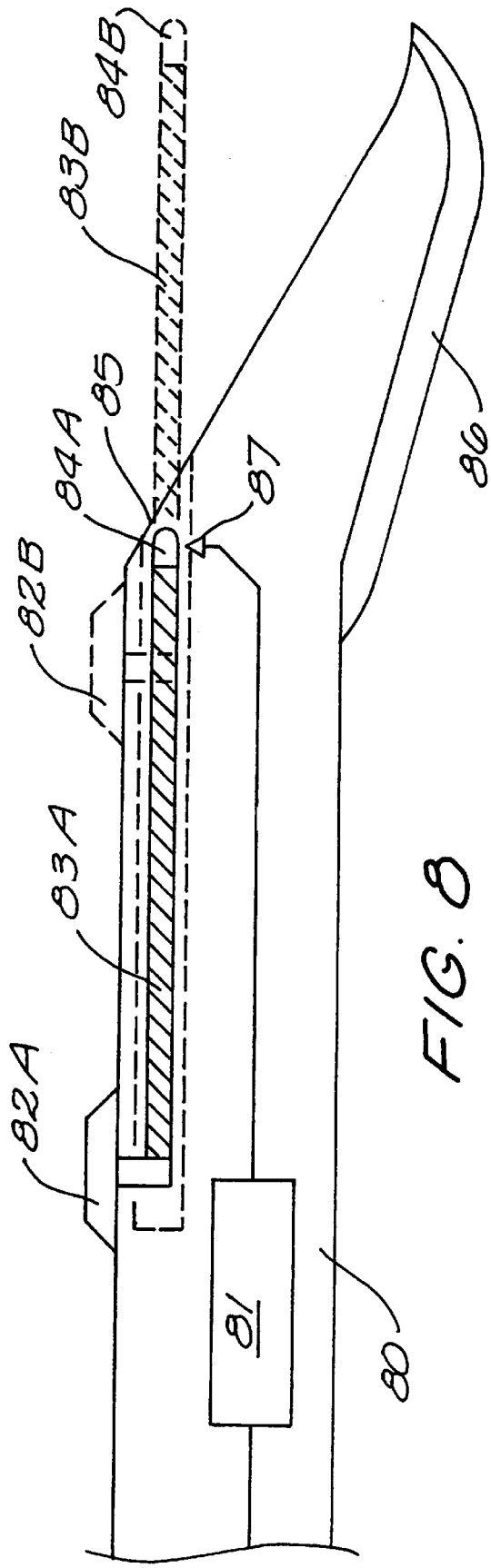
FIG. 8 is a view of an embodiment of the invention in which the nerve sensing probe is retractable into the housing when the probe is not in use.

FIG. 8 is a view of an embodiment of the invention in which the nerve sensing probe is retractable into the housing when the probe is not in use.

Housing 80 includes a scalpel portion 86. In this embodiment, cavity 85 is provided for containing probe 83A when not in use. Probe 83A is a rigid member with exposed contact 84A located at a tip.

When the surgeon desires to probe and identify nerve locations, the surgeon pushes slide button 82A forward into position 82B. Slide button 82A engages probe 83A so that as slide button 82A moves, so does probe 83A. Hence, when the slide button is in the position indicated by slide button 82B, the probe is in the position of 83B which presents the contacts as shown by contact 84B for use by the surgeon.

Further, as the surgeon moves the slide button 82A, contact/switch 87 is engaged. Contact/switch 87 provide an electrical contact between the electronics 81 and probe 83B and also closes a switch to activate electronics 81. In this manner, the electronics are dormant until the probe is fully extended.

In this embodiment, a light is provided within slide switch 82A with two different colors. A green light from slide switch 82B indicates that the apparatus is activated; a flashing red light indicates that a nerve has been sensed.

This embodiment is particularly useful since it permits the probe to be withdrawn, giving the surgeon a full view of scalpel 86.

It is clear that the present invention creates a highly improved surgical instrument.

What is claimed is:

1. A manually operated surgical instrument comprising:
   a) a housing having,
      1) a grip portion adapted to be held by a user, and,
      2) a distal end adapted for cutting tissue within a human body; and,
   b) an electronics unit contained within said housing and having,
      1) a first electrical lead adapted to be in electrical communication with the human body,
      2) means for generating a predefined shaped signal in said first electrical lead, for detecting the present of non-stimulated naturally occuring electrical signal from human nerves
      3) the second electrical lead having a contact proximate to a distal end of said manually operated instrument and adapted to electrically engage the human body,
      4) means for sensing the predefined shaped signal in said second electrical lead, and,
      5) alarm means for generating an alarm in response to sensing the predefined shaped signal in said second electrical lead.

2. The surgical instrument according to claim 1, wherein the distal end includes a pair of hinged blades and wherein said alarm means includes, in response to said predefined signal in said second electrical lead, means for blocking said hinged blades from closing.

3. The surgical instrument according to claim 1 wherein said electronics unit further includes means for electrically isolating said means for sensing from remote electronic systems.

* * * * *